(12) United States Patent
Williamson

(10) Patent No.: US 10,600,300 B2
(45) Date of Patent: Mar. 24, 2020

(54) IMPROVEMENTS TO MULTI-POINT SAMPLING VALVES

(71) Applicant: Xtralis Global, Dublin (IE)

(72) Inventor: Alasdair James Williamson, Worthing (GB)

(73) Assignee: XTRALIS GLOBAL, Dublin (IE)

( * ) Notice: Subject to any disclaimer, the term of this patent is extended or adjusted under 35 U.S.C. 154(b) by 734 days.

(21) Appl. No.: 15/036,461

(22) PCT Filed: Nov. 14, 2014

(86) PCT No.: PCT/EP2014/074602
§ 371 (c)(1),
(2) Date: May 13, 2016

(87) PCT Pub. No.: WO2015/071409
PCT Pub. Date: May 21, 2015

(65) Prior Publication Data
US 2016/0300466 A1    Oct. 13, 2016

(30) Foreign Application Priority Data

Nov. 14, 2013  (AU) .................................. 2013904413

(51) Int. Cl.
| | |
|---|---|
| *G08B 17/117* | (2006.01) |
| *G01N 1/26* | (2006.01) |
| *G08B 17/10* | (2006.01) |
| *G08B 17/113* | (2006.01) |
| *G08B 21/14* | (2006.01) |
| *G01N 1/24* | (2006.01) |

(52) U.S. Cl.
CPC ............. *G08B 17/117* (2013.01); *G01N 1/24* (2013.01); *G01N 1/26* (2013.01); *G08B 17/10* (2013.01); *G08B 17/113* (2013.01); *G08B 21/14* (2013.01)

(58) Field of Classification Search
CPC .................................. G01N 1/24; G01N 1/26
See application file for complete search history.

(56) References Cited

U.S. PATENT DOCUMENTS

| | | | | |
|---|---|---|---|---|
| 3,678,487 A | * | 7/1972 | Ludewig, Jr. | ........ G01N 15/065 340/507 |
| 3,757,583 A | * | 9/1973 | Ludewig, Jr. | ............ G01N 1/26 137/625.11 |
| 4,601,211 A | * | 7/1986 | Whistler | .................. G01N 1/26 137/554 |
| 5,164,604 A | * | 11/1992 | Blair | ....................... G01N 21/53 250/574 |

(Continued)

FOREIGN PATENT DOCUMENTS

| | | |
|---|---|---|
| DE | 32 37 021 A1 | 5/1983 |
| GB | 2 243 475 A | 10/1991 |

*Primary Examiner* — Natalie Huls
(74) *Attorney, Agent, or Firm* — Brooks, Cameron & Huebsch, PLLC

(57) ABSTRACT

A rotary sampling valve for a multi-point aspirated gas or smoke detection system, the rotary sampling valve including multiple sets of inlet ports, whereby, in a first operation mode, air is drawn via all inlet points simultaneously and, in a second operation mode, air is drawn via one inlet port from each set of inlet ports simultaneously. A multi-point aspirated gas or smoke detection system including a rotary sampling valve is also described.

16 Claims, 6 Drawing Sheets

(56) References Cited

U.S. PATENT DOCUMENTS

| | | | | |
|---|---|---|---|---|
| 5,926,098 | A * | 7/1999 | Wiemeyer | G08B 17/113 |
| | | | | 250/573 |
| 6,125,710 | A * | 10/2000 | Sharp | G01N 1/26 |
| | | | | 73/863.01 |
| 9,880,077 | B2 * | 1/2018 | Yoo | G01N 15/06 |
| 2004/0145484 | A1 | 7/2004 | Wagner et al. | |
| 2015/0022363 | A1 * | 1/2015 | Lang | G08B 17/10 |
| | | | | 340/628 |
| 2016/0266082 | A1 * | 9/2016 | Remondini | G01N 33/0031 |
| 2018/0095013 | A1 * | 4/2018 | Yoo | G01N 1/2273 |

* cited by examiner

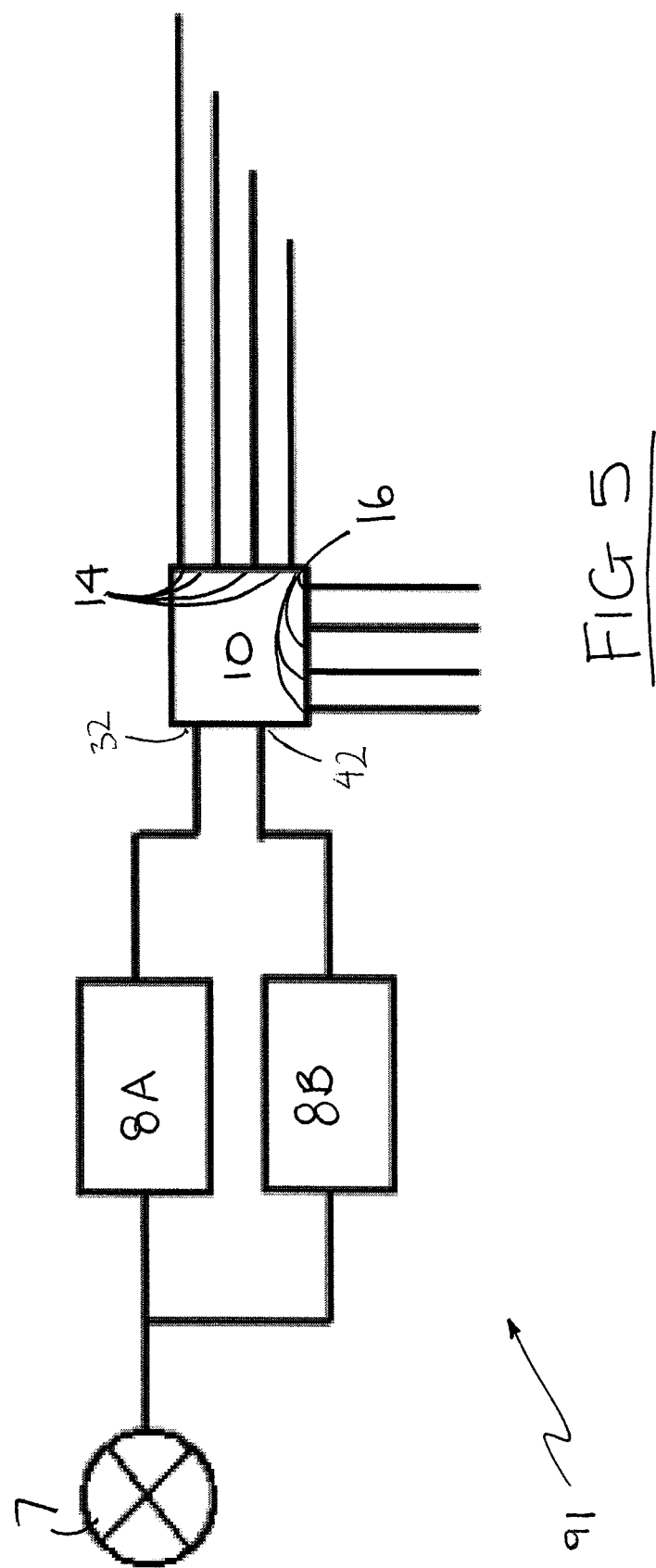

IMPROVEMENTS TO MULTI-POINT SAMPLING VALVES

FIELD OF THE INVENTION

The invention is directed to rotary sampling valves for a multi-point aspirated gas or smoke detection systems.

BACKGROUND OF THE INVENTION

Pollution monitoring, and fire protection and suppressant systems may operate by detecting the presence of smoke and other airborne pollutants. Upon a threshold level of particles being detected, an alarm or other signal may be activated and operation of a fire suppressant system and/or manual intervention may be initiated.

As illustrated in FIG. 1A, air sampling pollution monitoring equipment in the form of aspirated particle detection systems (1) may incorporate a sampling pipe network (2) consisting of one or more sampling pipes (3, 4, 5, 6) with one or more sampling holes, or inlets (3A, 4A, 5A, 6A), installed at positions where smoke or pre-fire emissions may be collected from a region or environment being monitored, which is ordinarily external to the sampling pipe network. Air is drawn in through the sampling holes and subsequently along the pipe or pipe network (2) by means of an aspirator or fan (7) and is directed through a detector (8) at a remote location. Sampling points in the form of the sampling inlets are located at regions where particle detection is required. These regions are typically distant from the actual detector. Although there are a number of different types of particle detectors which may be used as the detector in a system as outlined above, one particularly suitable form of detector for use in such a system is an optical scatter detector, which is able to provide suitable sensitivity at reasonable cost. An example of such a device is a VESDA® LaserPlus™ smoke detector as sold by the applicant. Multi-tube aspirated gas or smoke alarm systems such as that illustrated in FIG. 1A enable early detection of a smoke and/or gas event, and also the ability to quickly locate the source of such an event.

One such system is shown in GB 2243475B which describes a rotary air selector valve that enables rapid detection of an event followed by rapid location of the source and also gives the ability to capture transient events and to distinguish between transient and continuing events. Such a valve 9, as indicated, is used in the system of FIG. 1A to connect the multiple sampling pipes 3, 4, 5, 6 to the detector 8. In operation, air from different zones is directed from inlet tubes through the valve to a common gas or smoke detector 8. Upon detection of gas or smoke, an alarm is energized and the valve is operated to successively direct air from each tube to the detector so as to enable location of the zone giving rise to the gas or smoke.

Conventional multi-point gas or smoke sampling systems employ individually operated valves combined on a manifold or rotary valves, such as the type described above, allowing several tubes to be scanned sequentially with one device.

Where the number of tubes to be sampled is high then the cost and/or space requirements of the individual valving systems or multiple rotary valves becomes prohibitive.

The present invention aims to at least in part alleviate problems associated with prior multi-tube aspirated gas and smoke alarm systems, as well as providing a cost effective and efficient monitoring system.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The invention is based on a single rotary valve mechanism that has a plurality of sampling chambers allowing a large number of sampling tubes to be monitored efficiently.

According to a first aspect, the present invention provides a rotary sampling valve for a multi-point aspirated gas or smoke detection system, the rotary sampling valve having a plurality of sampling chambers, each chamber connecting a plurality of inlet ports to a respective common outlet.

According to a second aspect, the present invention provides a rotary sampling valve for a multi-point aspirated gas or smoke detection system, the rotary sampling valve including multiple sets of inlet ports, whereby, in a first operation mode, air is drawn via all inlet ports simultaneously and, in a second operation mode, air is drawn via one inlet port from each set of inlet ports simultaneously.

Advantageously, the first operation mode configures the inlet ports of each set of inlet ports to communicate with a corresponding common sampling chamber through which air is drawn to a corresponding outlet. The second operation mode configures a selected inlet port to connect with said corresponding outlet. In the second operation mode the inlet ports from within the set are sequentially selected to connect with said corresponding outlet.

According to a third aspect, the present invention provides a rotary sampling valve for a multi-point aspirated gas or smoke detection system, the rotary sampling valve including:
  a plurality of flow networks, each flow network having:
    a set of inlet ports;
    a common outlet; and
    a sampling chamber;
    whereby each flow network can be selectably configured to define a first flow path or one of a plurality of second flow paths, wherein the first flow path draws air into the flow network from each of the inlet ports to the common outlet via the sampling chamber, and wherein the second flow paths draw air into the network via a respective selected single inlet port to the common outlet;
  wherein the plurality of flow networks can each be configured to define the first flow path simultaneously.

Preferably, the second flow paths bypass the sampling chamber. The second flow paths can be sequentially defined by aligning an inlet in a rotor with a selected inlet port on a stator.

The valve may comprise a stator with one or more rotors rotationally connected thereto. The rotor and stator are preferably shaped to form the sampling chambers between them. The stator preferably includes the inlet ports and the outlets.

The inlet ports may be arranged in two or more concentric rings, each ring defining a set of inlet ports. The sampling chambers are preferably concentric annular or partially annular chambers.

The inlet ports may extend through a section of the stator to define a channel having a first opening and a second opening, wherein the first opening is of greater diameter than the second opening. The inlet ports are preferably each connected to a separate sampling tube, advantageously at the first opening. In one configuration, the inlet ports around one of the concentric rings have first openings that are radially offset and second openings that are positioned at a common radial distance.

According to a fourth aspect, the present invention provides a multi-point aspirated gas or smoke detection system including a rotary sampling valve according to any of the above aspects, and at least one particle counter, smoke detector or gas analyser.

In one embodiment, each flow network is in communication with a separate particle counter, smoke detector or gas analyser.

In an alternative embodiment, a single particle counter, smoke detector or gas analyser is connected to all of the sampling chambers in a first operation mode until particles are detected above a threshold level, the system then switches to a second operation mode, wherein sequential sampling is performed on a selected sampling chamber or chambers until a signal is found, then the system switches to a third operation mode, where each inlet port in the identified sampling chamber is sequentially sampled until a signal is identified.

BRIEF DESCRIPTION OF THE DRAWINGS

The invention will now be described, by way of example only, with reference to the accompanying drawings in which:

FIG. 5 illustrates a multi-point aspirated gas or smoke detection system according to one aspect of the present invention.

DETAILED DESCRIPTION OF THE EMBODIMENTS

Figure 1A:
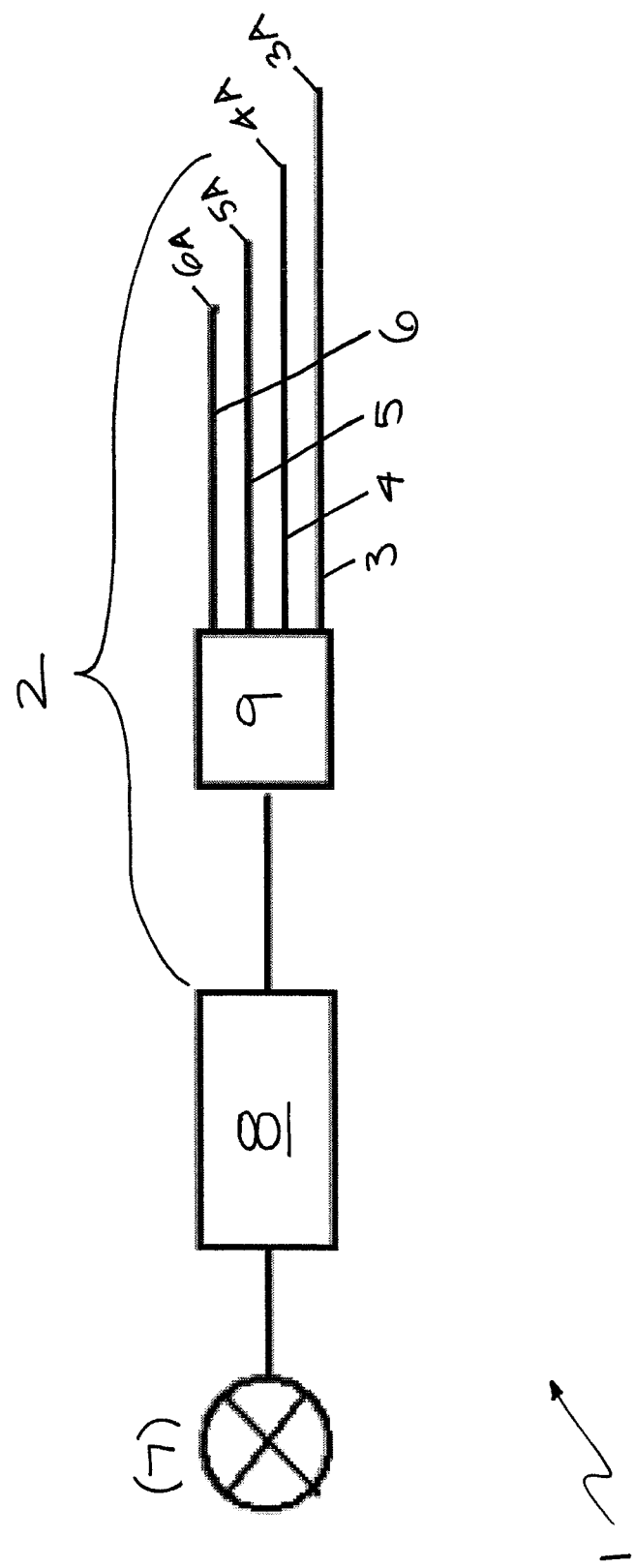
FIG. 1A illustrates an aspirated particle detection system according to the prior art.
Figure 1B:
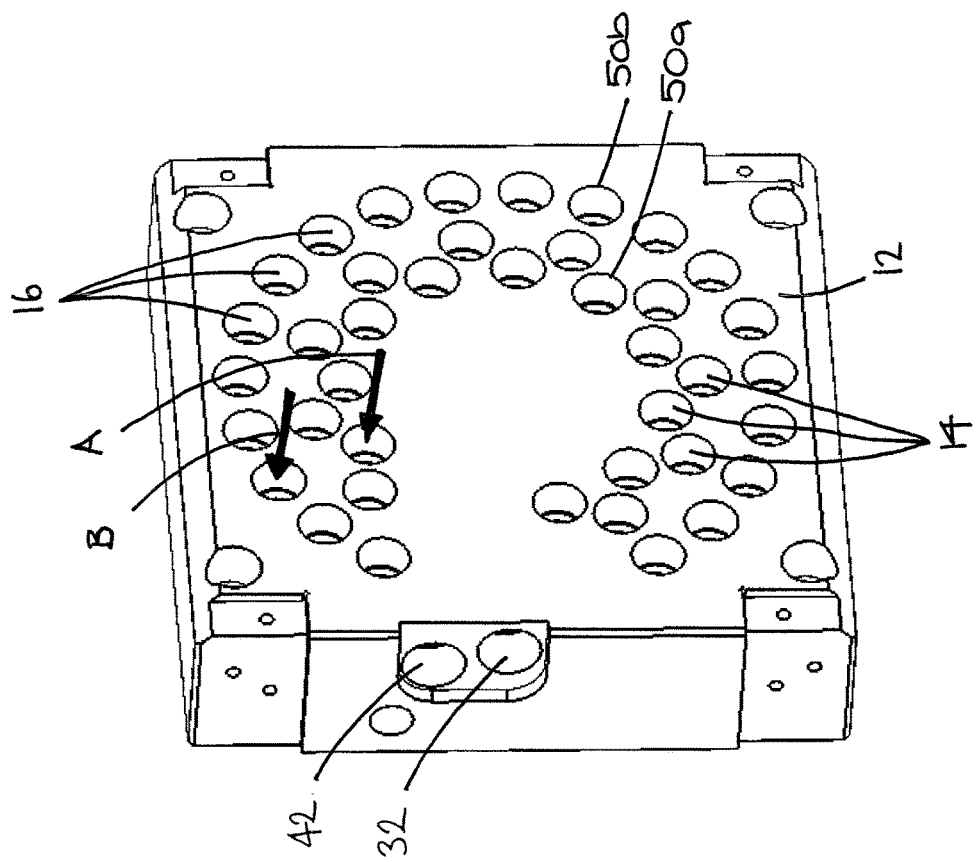
FIG. 1B illustrates an exploded view of the sampling valve from a first side according to an embodiment of the invention.
Figure 1B:
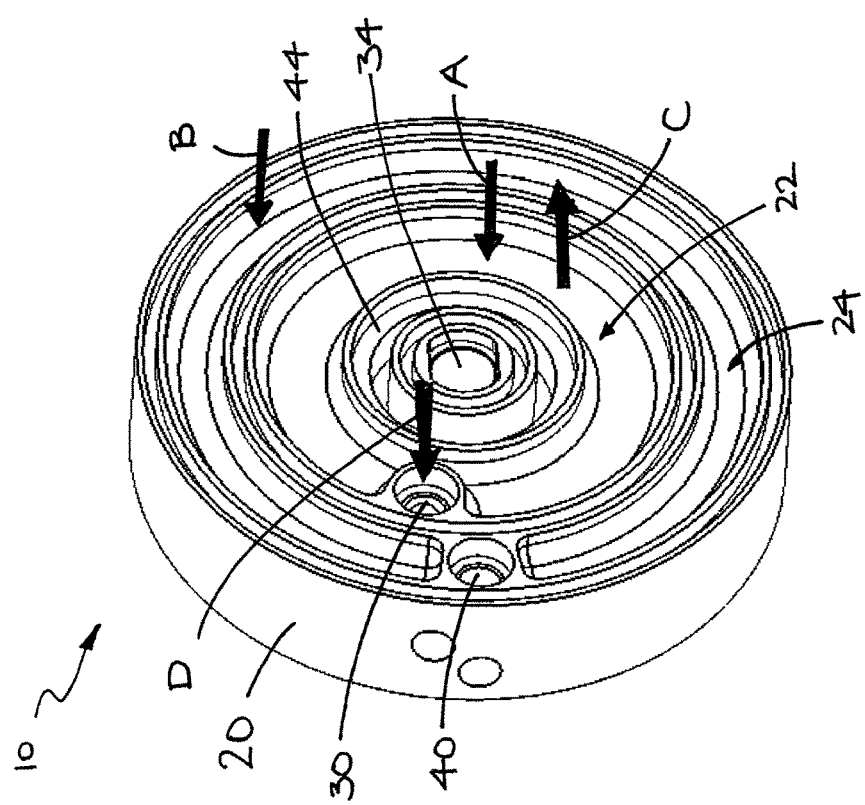

FIG. 1B shows an exploded view of a rotary sampling valve 10 in accordance with a preferred embodiment of the invention. The rotary sampling valve 10 is intended for use with a sampling pipe network (not shown) as described in the introduction. An aspirator (not shown) draws air through the sampling pipe network to and through the rotary sampling valve 10, and then to a detector (not shown). The detector may be any type of particle detector, comprising for example a particle counting type system such as a VESDA® LaserPlus™ smoke detector sold by the applicant. Typically the detector comprises a detection chamber, indicator means and an aspirator for drawing sampled air into the detection chamber. The illustrated embodiment is a forty channel example of the invention. In overview, the valve 10 includes a rotor 20 and a stator 12. The rotor 20 is rotatably mounted to the stator and can be rotated to select a mode of operation of the valve 10. The stator 12 has two concentric circular sets of inlet ports 14, 16. The forty pipes being sampled are connected to the inlet ports 14, 16, twenty pipes in each set.

Rotor 20 defines the voids for two sampling chambers, 22, 24 each in fluid communication with a set of twenty sample pipes, such that a first set of inlet ports 14 lead into the first, inner sampling chamber 22 and a second set of inlet ports 16 lead into the second, outer sampling chamber 24. The stator 12 closes the chambers, with various O-ring seals (not shown) sealing the various chambers and channels.

According to the illustrated embodiment, in a first operation mode, being a normal sampling mode, first flow paths are defined where air is continuously drawn from all inlet ports 14, 16 simultaneously. The air from ports 14 is channeled into inner chamber 22 and the air from ports 16 is channeled into outer chamber 24, as per arrows A and B in FIG. 1B. The air from inner chamber 22 then travels through the arc shaped port 26 in the stator 12 in the direction of arrow C. Port 26 is connected to port 28 via a duct (not shown) in the stator 12. Thus, sample air entering port 26 comes out of port 28 in the stator, which, in this first operation mode, is aligned with port 30 in the rotor 20; the air travelling in the direction of arrow D. Port 30 is in communication with the outlet 32 via central channel 34 to deliver the sampled air to the detector (not shown). Simultaneously, the air from outer chamber 24 travels through two ports 36 in the stator 12 via an internal duct, and out of port 38, which is aligned with port 40 in the rotor 20, the air then travelling to outlet 42 via annular channel 44. In this first operation mode air from all inlet ports of each set 14, 16 of inlet ports are sampled simultaneously. The first set of inlet ports 14, combined with the inner chamber 22 and the outlet ports 32 and connecting ducts together form a first flow network. The second set of ports 16, combined with the outer chamber 24 and the outlet 42 and connecting ducts together form a second flow network. These two flow networks are typically kept isolated from each other such that detection of particles in a sample from one flow network allows the identification of the flow network to thereby enable the subsequent identification of the relevant sample tube that was the source of the detected particles.

When gas or smoke is detected with the rotary valve 10 in the first configuration shown in FIG. 1B the rotor 20 enters a second operation mode in which second flow paths are defined. Each second flow path connects an inlet port from each set of ports 14, 16 to the detector. The selection of inlet ports is performed sequentially in each flow network to enable the level of gas or smoke present in each sampling tube to be determined. In the example illustrated, both sets of inlet ports 14, 16 are scanned simultaneously with a common rotor 20. This is done by directly aligning the ports 30 and 40 on the rotor 20 with respective inlet ports of each set 14, 16 such that the sampling chambers are effectively bypassed. In this second operation mode, the air from the one selected inlet port of set 14 from the first network flows directly into port 30, out central channel 34 to outlet 32. Simultaneously, air from one selected inlet port of set 16 from the second network flows directly into port 40 and out annular channel 44 to outlet 42. Once a sample from these respective inlet ports is analysed by a detector, the rotor 20 is rotated to align the ports 30, 40 with a subsequent pair of inlet ports from each set 14, 16. This stepped rotation is continued until all ports are scanned and the sampling tube(s) drawing smoke, particles or gas is identified.

It will be appreciated that each circular array of inlet ports 14, 16 may be scanned individually with the use of concentric rotors (not illustrated) that operate independently.

Figure 2:
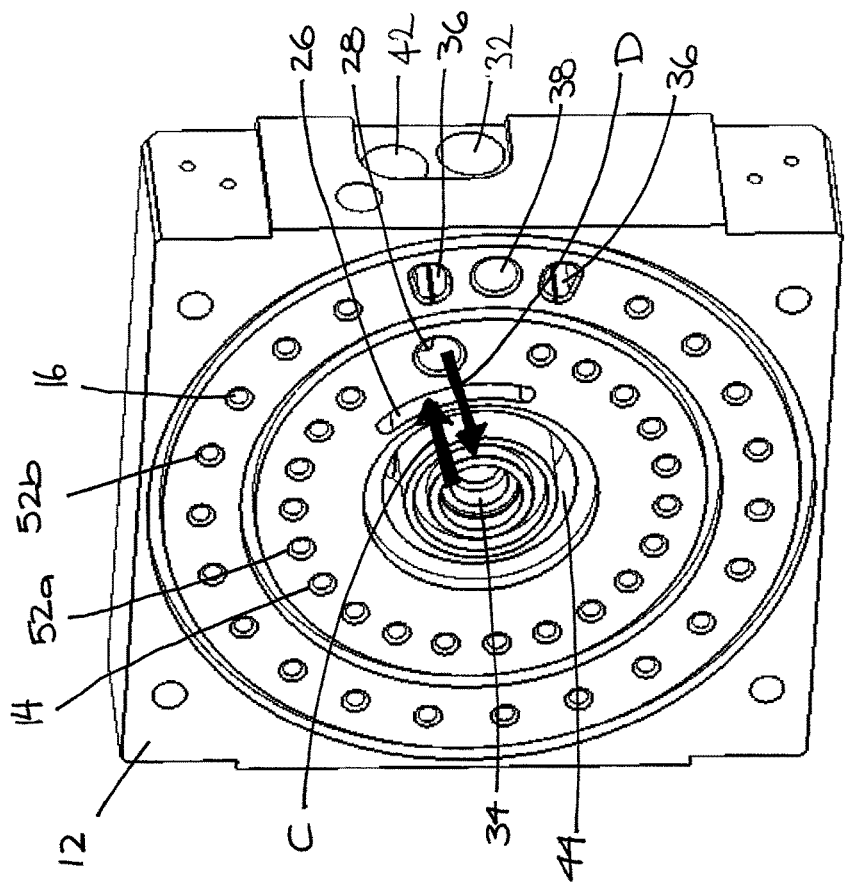
FIG. 2 illustrates an exploded view of the sampling valve of FIG. 1B from a second side.
Figure 2:
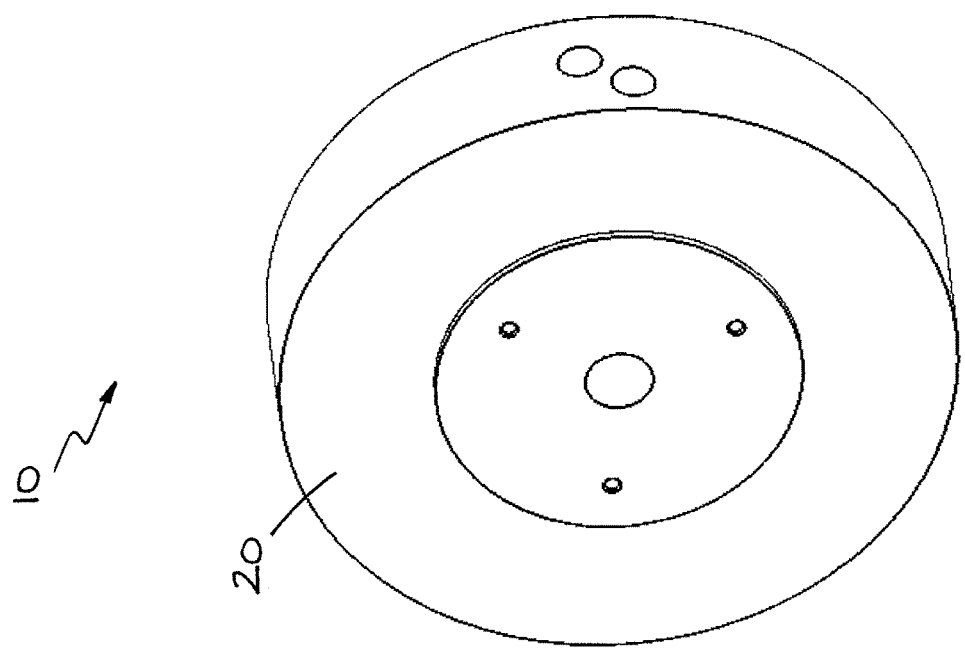
Figure 3:
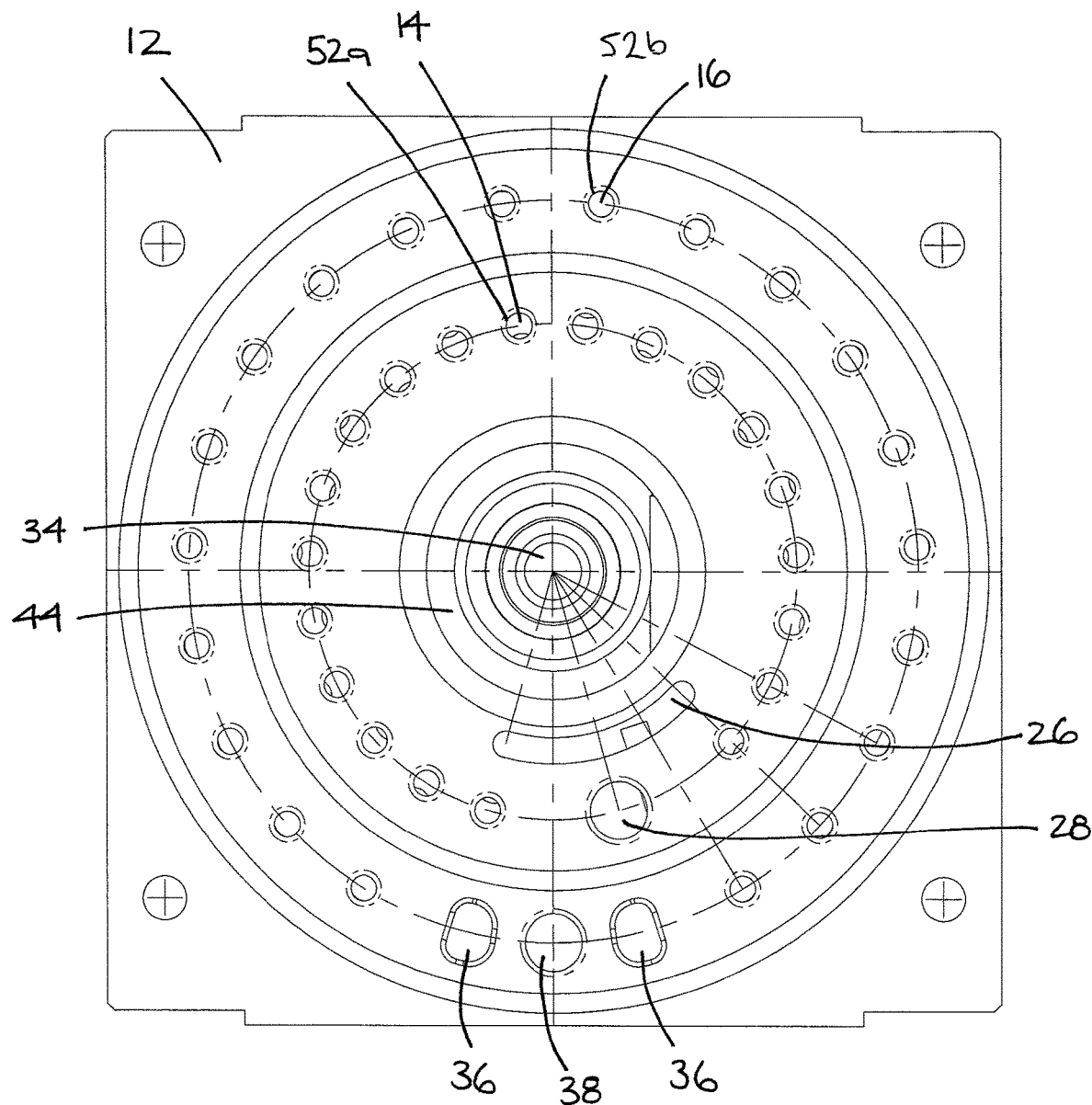
FIG. 3 illustrates a diagrammatic plan view of the inner face of the rotor.
Figure 4:
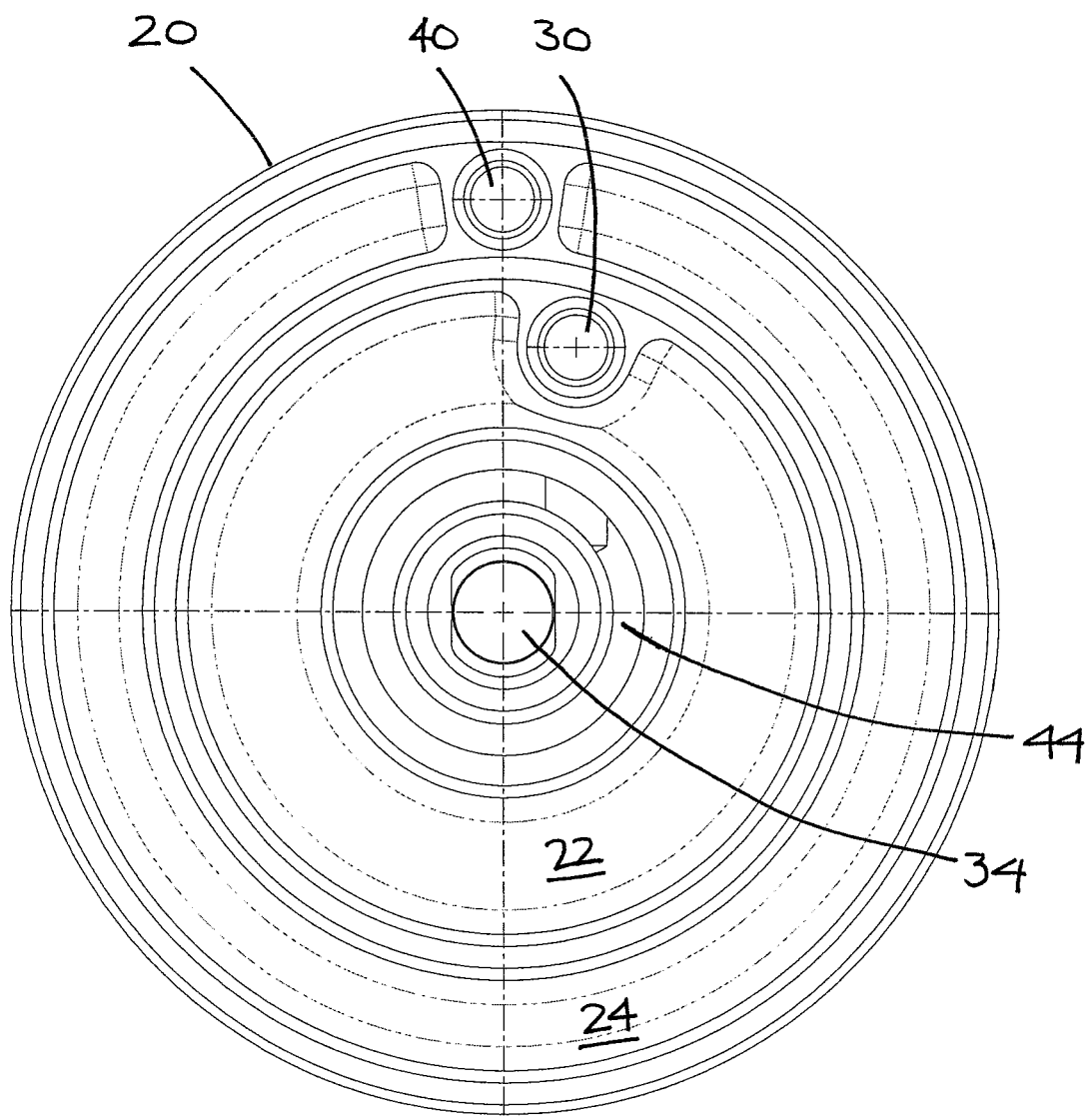
FIG. 4 illustrates a diagrammatic plan view of the inner face of the stator.

As shown in FIGS. 1B and 3, the inlet ports of the sets 14, 16 extend through the stator 12 to form a channel and therefore have a first opening 50a, 50b and a second opening 52a, 52b on the opposite side of the stator 12. It can be seen from the Figures that the first openings 50a, 50b have a greater diameter than the second openings 52a, 52b, such that the diameter of the channels is stepped down internally. As shown in FIGS. 2 and 3, this results in the second openings 52a, 52b of each set 14, 16 being positioned at a common radial distance to align with the rotor ports 30, 40. The spacing of the second openings 52b of the second set of twenty ports 16 (being the outer circle) is such that the distance between each first opening 50b can be evenly spaced at a common radial distance, with the centre of the first opening 50b being axially aligned with the second opening 52b. However, to maintain the alignment of the second openings 52a of the first set with the second openings 52b of the second set, as shown best in FIG. 3, the internal step is axially offset in ports 14, such that the centre of the first opening 50a is not aligned with the centre of the second opening 52a, as best shown in FIG. 1B. To maximise the number of ports in the set 14 arranged as the inner circle, every second first opening 50a is offset in an opposite direction, one radially inwards, one radially outwards from the circumferential line of the second openings 52a.

FIG. 5 schematically illustrates one embodiment of a multi-point aspirated gas or smoke detection system using a valve 10 of the type described above. The system 91 includes a plurality of detectors 8A, 8B connected to a single air movement device 7, such as a pump, aspirator or fan. Each detector 8A and 8B is connected to a respective outlet 32, 42 of the sampling valve 10. The outlet 32 is fed by sampling tubes connected to the set of inlet ports 14 and the outlet 42 is fed by sampling tubes connected to the set of inlet ports 16. As described above the system operates in a first mode where the detectors 8A and 8B are each provided air samples that are derived from the full set of sampling tubes connected to their corresponding inlet port sets 14, 16. When one of the detectors detects particles or gas at a predetermined level the system moves to a second mode of operation where the valve 10 sequentially connects each inlet pipe to its corresponding outlet to enable an identification of which pipe (or pipes) are drawing smoke or gas.

According to one embodiment, once the source of the smoke, particles or gas has been identified the sample drawn from the identified pipe can be diverted (using a valve not shown) into both detectors. This allows both detectors to analyse a sample from the same source. This can be used to confirm the initial detection event. In such an embodiment the detectors can be arranged in a 'double knock' configuration such that the overall system is less susceptible to false alarms.

According to another embodiment, a single detector could be connected to multiple outlets of a valve of the type described above. The connection can be made via one or more valves (preferably arranged in stages) that can selectively combine flows from two (or more pipes) or enable all flows to proceed in a single outlet. In this arrangement the detector can initially receive a mixture of sample air from all sets of inlets simultaneously. Upon initial detection a first stage selector valve can be used to determine which of its inlets is providing smoke, particles or gas by alternately directing its different flows to its outlet. If the rotary valve has a high number of outlets, multiple stages of selector valves can be used. Preferably the valves can be arranged so that a search of the rotary valve's chambers can be done in an optimised binary exclusive search where half the chambers are searched, followed by a quarter and so on until the chamber(s) in alarm are located. Once the search for the source of the smoke, gas or particles has been narrowed to a single chamber of the valve the valve can be used to sequentially couple each of its inlets to its outlet to allow final determination of the source of the particles, smoke or gas.

The present invention enables a multi-point aspirated gas or smoke detection system to connect to more sampling tubes, typically more than double, with a single valve. This greatly reduces manufacturing costs.

It will be understood that the invention disclosed and defined in this specification extends to all alternative combinations of two or more of the individual features mentioned or evident from the text or drawings. All of these different combinations constitute various alternative aspects of the invention.

I claim:

1. A rotary sampling valve for a multi-point aspirated gas or smoke detection system, the rotary sampling valve including:
   a stator and one or more rotors, being shaped to form a plurality of sampling chambers between them;
   wherein a plurality of flow networks are defined, each flow network having:
      a set of inlet ports;
      a common outlet;
      and a sampling chamber;
   whereby each flow network can be selectably configured to define a first flow path or one of a plurality of second flow paths, wherein the first flow path draws air into the flow network from each of the inlet ports to the common outlet via the sampling chamber, and wherein the second flow paths draw air into the network via a respective selected single inlet port to the common outlet;
   wherein the plurality of flow networks can each be configured to define the first flow path simultaneously.

2. A rotary sampling valve for a multi-point aspirated gas or smoke detection system, the rotary sampling valve including:
   a stator and one or more rotors, being shaped to form a plurality of sampling chambers between them;
   multiple sets of inlet ports; and
   a plurality of outlets;
   wherein a plurality of flow networks are defined, each flow network having:
      one of said sets of inlet ports;
      one of said sampling chambers; and
      one of said outlets;
   whereby each flow network can be selectably configured in a first operation mode to define a first flow path or in a second operation mode to define one of a plurality of second flow paths, wherein the first flow path draws air into the flow network from each of the inlet ports of said set of inlet ports to one of said outlets via a corresponding one of said sampling chambers, and wherein the defined second flow path draws air into the network via a respective selected single inlet port of said set of inlet ports to one of the outlets;
   wherein the plurality of flow networks are isolated from each other and, in the first operation mode, the plurality of flow networks can each be configured to define a corresponding said first flow path simultaneously such that air is drawn via all inlet ports of said multiple sets of inlet ports simultaneously and, in the second operation mode, the plurality of networks can each be configured to define corresponding one of said plurality of second flow paths simultaneously, such that air is drawn via one inlet port from each set of inlet ports simultaneously, such that detection of particles in a sample from one flow network allows the identification of a corresponding flow network to thereby enable the subsequent identification of the relevant inlet port that was the source of the detected particles.

3. The valve of claim 2, wherein each of the second flow paths bypass a corresponding sampling chamber.

4. The valve of claim 2, wherein each of the second flow paths can be sequentially defined by aligning an inlet in said one or more rotors with a selected inlet port on said stator.

5. The valve of claim 2 comprising said stator with more than one said rotor rotationally connected thereto.

6. The valve of claim 5, wherein the stator includes the inlet ports and the outlets.

7. The valve of claim 6, wherein the inlet ports are arranged in two or more concentric rings, each ring defining a set of inlet ports.

8. The valve of claim 7, wherein the sampling chambers are concentric annular or partially annular chambers.

9. The valve according to claim 7, wherein the inlet ports around one of the concentric rings have first openings that are radially offset and second openings that are positioned at a common radial distance.

10. The valve of claim 5, wherein the inlet ports extend through a section of the stator to define a channel having a first opening and a second opening, wherein the first opening is of greater diameter than the second opening.

11. The valve according to claim 10, wherein the inlet ports are each connected to a separate sampling tube at the first opening.

12. The valve according to claim 2, wherein each flow network is in communication with a separate particle counter, smoke detector or gas analyser.

13. A multi-point aspirated gas or smoke detection system including a rotary sampling valve according to claim 2, and at least one particle counter, smoke detector or gas analyser.

14. The system according to claim 13, wherein a single particle counter, smoke detector or gas analyser is connected to all of the sampling chambers in a first operation mode until particles are detected above a threshold level, the system then switches to a second operation mode, wherein sequential sampling is performed on a selected sampling chamber or chambers until a signal is found, then the system switches to a third operation mode, where each inlet port in the identified sampling chamber is sequentially sampled until a signal is identified.

15. A multi-point aspirated gas or smoke detection system including a rotary sampling valve as claimed in claim 2.

16. The valve of claim 2, wherein, in the second operation mode, the inlet ports from within the set are sequentially selected to connect with a corresponding outlet.

* * * * *